United States Patent [19]

Burrell et al.

[11] 4,059,703

[45] Nov. 22, 1977

[54] PESTICIDAL COMPOUNDS, PROCESSES AND COMPOSITIONS

[75] Inventors: Raymond Alexander Burrell, Camberley; John Michael Cox, Wokingham, both of England

[73] Assignee: Imperial Chemical Industries Limited, London, England

[21] Appl. No.: 712,378

[22] Filed: Aug. 6, 1976

[30] Foreign Application Priority Data

Aug. 19, 1975 United Kingdom ............... 34507/75

[51] Int. Cl.$^2$ .................... A61K 31/445; C07D 257/04

[52] U.S. Cl. ................................ 424/269; 260/308 D

[58] Field of Search ..................... 424/269; 260/308 D

[56] References Cited

U.S. PATENT DOCUMENTS 3,830,928 8/1974 Mrozik ................................ 424/269

OTHER PUBLICATIONS

*Merck Index*, 7th ed., (1960), p. 1468, Merck & Co., Rahway, N.J. U.S.A.

*Primary Examiner*—Frederick E. Waddell

*Attorney, Agent, or Firm*—Cushman, Darby & Cushman

[57] ABSTRACT

Pesticidal tetrazole derivatives having the formula:

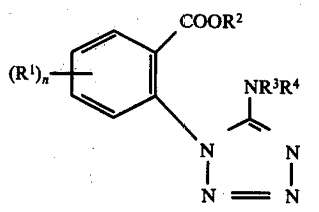

wherein $n$ is 0, 1, 2, 3 or 4; $R^1$ is OH, halogen, alkyl, alkoxy, alkylthio, alkylsulphonyl, $NO_2$, $NH_2$ (optionally substituted), acyl, aroyl, CN, carboxy or sulphonic-acid or -ester or -amide; $R^2$ is hydrogen or optionally-substituted alkyl; $R^3$ and $R^4$ are hydrogen or optionally-substituted alkyl, aryl, cycloalkyl or acetyl but $R^4$ is not aryl or cycloalkyl if $R^3$ is one of these two groups; and salts thereof when $R^2$ is hydrogen.

7 Claims, No Drawings

PESTICIDAL COMPOUNDS, PROCESSES AND COMPOSITIONS

This invention relates to pesticidal 1-phenyl- 5-amino-tetrazoles. More particularly, the invention relates to methods for combating pests, especially fungi, compositions therefor and to novel 1-phenyl-5-amino-tetrazoles and processes for preparing them.

The present invention provides novel tetrazole derivatives having the formula:

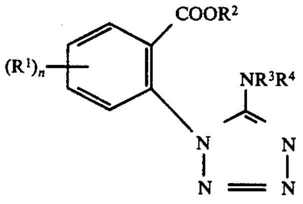

wherein $n$ is zero or an integer of 1 to 4 and each $R^1$ is selected from hydroxy, halogen, alkyl, alkoxy, alkylthio, alkylsulphonyl, nitro, amino, substituted amino, acyl, aroyl, cyano, carboxy or sulphonic acid or ester or amide; $R^2$ is hydrogen or optionally-substituted alkyl; $R^3$ and $R^4$ are hydrogen or optionally-substituted alkyl, cycloalkyl, aryl or acetyl groups provided that when $R^3$ is aryl or cycloalkyl $R^4$ is other than either of these two groups; and salts thereof when $R^2$ is hydrogen.

In particular this invention provides compounds having the structural formula:

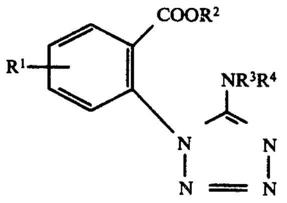

Where $R^1$ is hydrogen or chlorine, $R^2$ and $R^3$ are hydrogen or alkyl containing 1 to 4 carbon atoms; $R^4$ is hydrogen, alkyl containing from 1 to 4 carbon atoms (especially methyl), cycloalkyl or acetyl; and salts thereof.

The amide-esters ($R^2$ = lower alkyl; $R^3$ = alkyl, cycloalkyl; $R^4$ = acetyl) may be prepared by a base catalysed Smiles rearrangement of the corresponding 5-N-alkylacetylaminomethane sulphonyltetrazole. Further hydrolysis can give the amino-acids ($R^2 = R^3 = H$, $R^4$ = alkyl, cycloalkyl) although, in many cases, these are better made by the hydrolysis of the corresponding 4-substituted-4,5-dihydrotetrazolo [1,5-a]quinazolin-5-one. Dialkylamino esters can be made, for example, by alkylation of alkylamino acids and further hydrolysed to dialkylaminoacids ($R^2$ = H; $R^3$ and $R^4$ = alkyl).

In so far as these methods are new, or are applied to the preparation of the novel compounds defined herein, they form part of the present invention.

The present invention further provides pesticidal compositions comprising as an active ingredient a tetrazole derivative having the formula:

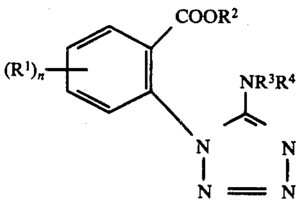

wherein $n$ is zero or an integer of 1 to 4 and each $R^1$ is selected from hydroxy, halogen, alkyl, alkoxy, alkylthio, alkylsulphonyl, nitro, amino, substituted amino, alkoxycarbonyl, acyl, aroyl, cyano, carboxy or sulphonic acid or ester or amide; $R^3$ and $R^4$ are hydrogen or optionally-substituted alkyl, aryl or acetyl groups provided that when $R^3$ is aryl or cycloalkyl, cycloalkyl $R^4$ is other than either of these two groups; or a salt thereof when $R^2$ is hydrogen.

In a further, preferred, aspect the invention provides pesticidal compositions comprising, as an active ingredient, a tetrazole derivative having the formula:

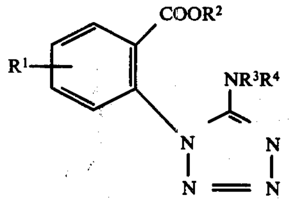

Where $R^1$ is hydrogen or chlorine, $R^2$ and $R^3$ are hydrogen or alkyl containing 1 to 4 carbon atoms; $R^4$ is hydrogen, alkyl containing from 1 to 4 carbon atoms (especially methyl), cycloalkyl or acetyl; or a salt thereof.

The present invention further provides a process for combating fungi which comprises treating fungi, crops, plants, or seeds, or any locus of any of these, with a tetrazole derivative having the formula:

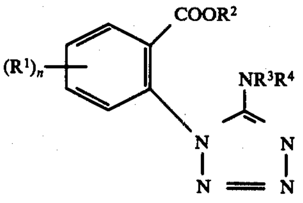

wherein $n$ is zero or an integer of 1 to 4 and each $R^1$ is selected from hydroxy, halogen, alkyl, alkoxy, alkylthio, alkylsulphonyl, nitro, amino, substituted amino, acyl, aroyl, cyano, carboxy, or sulphonic acid or ester or amide; $R^2$ is hydrogen or optionally-substituted alkyl; $R^3$ and $R^4$ are hydrogen, or optionally-substituted alkyl, cycloalkyl, aryl or acetyl, provided that when $R^3$ is aryl or cycloalkyl $R^4$ is other than either of these two groups; or a salt thereof when $R^2$ is hydrogen.

In a further, preferred, aspect the invention provides a process for combating fungi which comprises treating fungi, crops, plants or seeds, or any locus of these, with a tetrazole derivative having the formula:

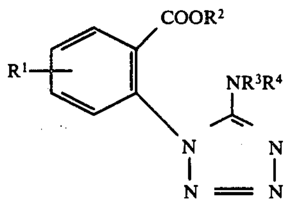

Where $R^1$ is hydrogen or chlorine, $R^2$ and $R^3$ are hydrogen or alkyl containing 1 to 4 carbon atoms; $R^4$ is hydrogen, alkyl containing from 1 to 4 carbon atoms (especially methyl), cycloalkyl or acetyl; or a salt thereof.

In carrying the invention process into practical effect pests, growing crops, plants, seeds, or soil, or any locus of any of the foregoing, may be treated by any of the well known and established procedures used in agriculture and crop protection.

Thus, for example, the active compound may be applied as solids, liquids, solutions, dispersions, emulsions and these may comprise, in addition to the active substance, any other adjuvant useful for formulation purposes, or any other biologically active substance, for example to increase the number of diseases combated.

Such solid or liquid substances and formulations may be applied, for example, by any conventional technique, for example by dusting, or otherwise applying the solid substances and formulations to the surfaces of growing crops, harvested produce, plants, seeds or soil, or to any part, or combination of parts thereof, or, for example, applying liquids or solutions for example, by dipping, spraying, mist blowing or soaking techniques.

The invention process is therefore useful for treating plants, seeds, harvested fruits, vegetables, or cut flowers infested with, or liable to infestation with any of the aforementioned specific fungal or bacterial diseases.

The term "seeds" is intended to include propagative plant forms generally and therefore includes, for example, cut stems, corms, tubers, rhizomes and the like.

The active compounds, or salts thereof, may be used as such but are preferably formulated into compositions for this purpose. Preferred compositions contain, as an active ingredient, the compounds prepared as described in the Examples hereinafter.

The compositions of the invention may be in the form of dusting powders or granules wherein the active ingredient is mixed with a solid diluent or carrier. Suitable diluents or carriers may be, for example, kaolin, bentonite, kieselguhr, dolomite, calcium carbonate, talc, powdered magnesia, Fuller's earth, gypsum, Hewitt's earth, diatomaceous earth and china clay. Compositions for dressing seed, for example, may comprise an agent assisting the adhesion of the composition to the seed, for example, a mineral oil.

The compositions may also be in the form of dispersible powders or grains comprising, in addition to the active ingredient, a wetting agent to facilitate the dispersion of the powder or grains in liquids.

Such powders or grains may include fillers, suspending agents and the like.

The compositions may also be in the form of liquid preparations to be used in the process of the invention for plants or harvested produce which are generally solutions, aqueous dispersions or emulsions containing the active ingredient in the presence of one or more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example, sodium lauryl sulphate, salts of sulphonated aromatic compounds, for example, sodium dodecylbenzensulphonate, sodium calcium or ammonium lignosulphonate, butyl-naphthalene sulphonate, and a mixture of the sodium salts of diisopropyl- and triisopropylnaphthalene sulphonic acids. Suitable agents of the non-ionic type include, for example, the condensation products of ethylene oxide with fatty alcohols such as oleyl alcohol or cetyl alcohol, or with alkyl phenols such as octylphenol, nonylphenol and octylcresol.

Other non-ionic agents are the partial esters derived from long chain fatty acids and hexitol anhydrides, the condensation products of the said partial esters with ethylene oxide, and the lecithins.

Suitable suspending agents are, for example, hydrophilic colloids, for example, polyvinylpyrrolidone and sodium carboxymethylcellulose, and the vegetable gums for example, gum acacia and gum tragacanth.

The aqueous solutions, dispersions or emulsions may be prepared by dissolving the active ingredient in an organic solvent which may contain one or more wetting, dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example, for improving the distribution, adhesive power and resistance to rain on treated surfaces, the different compositions can be better adapted for the various uses for which they are intended.

The compositions may also be conveniently formulated by admixing them with fertilisers. A preferred composition of this type comprises granules of fertiliser material incorporating an invention compound. The fertiliser material may, for example, comprise nitrogen, or phosphate-containing substances.

The compositions which are to be used in the form of aqueous dispersions or emulsions are generally supplied in the form of a concentrate containing a high proportion of the active ingredient, the said concentrate to be diluted with water before use.

The concentrates are often required to withstand storage for prolonged periods and after such storage, to be capable of dilution with water in order to form aqueous preparations which remain homogeneous for a sufficient time to enable them to be applied by conventional spray equipment.

The concentrates may conveniently contain from 10-85% and generally from 20-60% weight of the active ingredient. When diluted to form aqueous preparations, such preparations may contain varying amounts of the active ingredient depending upon the purpose for which they are to be used, but an aqueous preparation containing between 0.001% and 10% by weight of active ingredient may be used.

It is understood that the compositions of this invention may comprise, in addition to one or more active compounds according to the invention, one or more other substances having biological activity, for example, insecticidal, fungicidal, plant growth regulating, bactericidal or herbicidal activity.

This invention is illustrated, but not limited by, the following Examples, in which temperatures are expressed in degrees centigrade.

EXAMPLE 1

This example illustrates the preparation of 2(5'-methylaminotetrazol-1'-yl) benzoic acid having the structural formula:

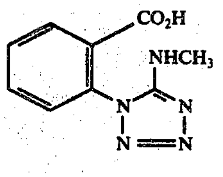

(Compound No. 1)

A mixture of 4-methyl-4,5-dihydrotetrazolo [1,5-a]quinazolin-5-one (2.4 g, prepared as described at the end of the present specific example) and N sodium hydroxide solution (24 ml) was refluxed, with stirring, for one hour. The clear solution was cooled, treated with diluted hydrochloric acid and the resultant precipitate washed with water and dried. Trituration with dichloromethane, to remove any unchanged starting material, gave the title compound (2.31 g, m.p. 155° ). It can be recrystallised from alcohol unchanged provided that conditions are neutral but heating in the presence of either acid or base causes reversion to the tetrazoloquinazolinone.

The preparation of 4-methyl-4,5-dihydrotetrazolo [1,5-a]quinazolin-5-one having the structural formula:

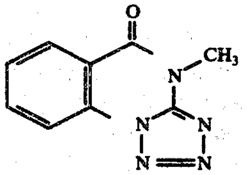

may be accomplished using any of the alternative processes described below:

a. A mixture of anthranilic acid (22.5 g), methyl isothiocyanate (12.5 g) and ethanol (200 ml) was refluxed for three hours, cooled and the precipitate filtered off and washed with water. Recrystallisation from ethanol gave 2-mercapto-3-methyl-3,4-dihydroquinazolin-4-one (13.0 g, m.p. 265°-266° ). A mixture of this material (5.76 g) hydrazine hydrate (20 ml) and ethanol (30 ml) was refluxed for 30 minutes, then cooled. The precipitate was filtered off, washed with water and dried to give the 2-hydrazinoquinazolinone (3.16 g, m.p. 220°-223° ). Recrystallisation from ethanol gave material m.p. 223°. A stirred solution of the crude product (1.9 g) in a mixture of hydrochloric acid (20 ml, 2N) and acetic acid (10 ml) was treated dropwise at 0°-5° with a solution of sodium nitrite (0.69 g) in water (5 ml). The mixture was allowed to attain room temperature and, after one hour, was filtered and the precipitate washed with water and dried to give the title compound (1.04 g, m.p. 164°-167°). Recrystallisation from ethanol gave material m.p. 167°.

OR b. A solution of 4,5-dihydrotetrazolo [1,5-a]quinazolin-5-one (1.8 g, prepared as described in Example 1) in dry N,N-dimethylformamide (20 ml) was added slowly to a suspension of sodium hydride (0.5 g, 50% suspension in mineral oil, prewashed with light petroleum) in dimethyl-formamide (10 ml). After 10 minutes methyl iodide (5 ml) was added and the mixture allowed to stand for 3 hours. It was then diluted with water and the precipitate washed with water and dried to give the title compound (1.9 g, m.p. 164°-166° ). Recrystallisation from ethanol gave material m.p. 167°.

OR c. A mixture of methyl 2-isothiocyanatobenzoate (19.0 g, prepared as described in *J. Org. Chem.*, 1962, 27, 3701), sodium azide (9.85 g) and water (200 ml) was refluxed, with stirring, for thirty minutes. It was then cooled, filtered through kieselguhr and acidified with dilute hydrochloric acid to give methyl 2(5'-mercaptotetrazol-1'-yl) benzoate (17.28 g, m.p. 147°-8° ).

A mixture of this material (11.35 g), sodium hydride (2.12 g, 50% dispersion in mineral oil, pre-washed with petroleum) and dry N,N-dimethylformamide (44 ml) was treated, with stirring at 0°, with N-methylchloroacetamide (5.24 g). It was stirred for 18 hours, poured into ice-water and the precipitate filtered off and dried. Recrystallisation from methanol gave methyl 2[5'- (N-methylacetamidomethylthio) tetrazol-1'-yl]benzoate (8.52 g, m.p. 97°-8° ).

A mixture of this material (7.0 g), acetic acid (58 ml), 2N sulphuric acid (58 ml) and potassium permanganate (5.8 g) was stirred at 5° for one hour, then decolorised by the addition of sodium metabisulphite. Water was added and the precipitate filtered off and washed with water. Recrystallisation from methanol gave methyl 2[5'-(N-methylacetamidomethanesulphonyl) tetrazol-1'-yl]benzoate (4.66 g, m.p. 138°-9°, decomp.).

A mixture of this material (3.4 g), 1,5- diazabicyclo-[4.3.0]non-5-one (1.2 g) and acetonitrile (28 ml) was refluxed for thirty minutes, cooled, diluted with water, acidified with dilute hydrochloric acid and extracted with chloroform. The extract was washed, dried and evaporated and the residue triturated with ether/petroleum and recrystallised from toluene to give methyl 2[5'-(N-acetylmethylamino)tetrazol-1'yl]benzoate (2.45 g, m.p. 134° ).

A solution of this compound (275 mg) in hot methanol (3 ml) was rapidly cooled and treated, at 5°, with N sodium hydroxide solution (6 ml). After stirring for five minutes, the mixture was filtered and the filtrate extracted with chloroform. The aqueous layer was acidified with dilute hydrochloric acid to give 2(5'-methylaminotetrazol-1-yl)benzoic acid (90 mg, m.p. 152°-4° ).

A mixture of this compound (90 mg), ethanol (2 ml) and N hydrochloric acid (0.1 ml) was refluxed for twenty minutes and cooled to give the title compound (60 mg, m.p. 166° ). It should be noted that this stage can also be catalysed by bases e.g. sodium hydroxide.

EXAMPLE 2

This example illustrates the preparation of 2(5'-methylaminotetrazol-1'-yl)benzoic acid by an alternative procedure to that described in Example 1.

A solution of methyl 2[5'-(N-acetylmethylaminotetrazol- 1'-yl]benzoate (275 mg; prepared as described in Example 4) in hot methanol (3 ml) was rapidly cooled and, at 5° treated with N sodium hydroxide solution (6 ml). After stirring for five minutes, the mixture was filtered and the filtrates extracted with chloroform. The aqueous layer was acidified with dilute hydrochloric acid to give the title compound (90 mg; m.p. 152°-4° ).

EXAMPLE 3

This example illustrates the preparation of sodium 2(5'-methylaminotetrazol-1'-yl)benzoate having the structural formula:

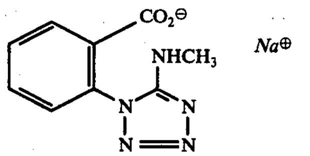

(Compound No 2)

A mixture of 4-methyl-4,5-dihydrotetrazolo [1,5-a]quinazolin-5-one (1.0 g), N sodium hydroxide solution (5.0 ml) and water (15 ml) was refluxed for one hour, cooled and extracted with chloroform. The aqueous layer was evaporated under reduced pressure and the residue triturated with acetone, then ether, to give the title compound (1.0 g, m.p. 245°-250°, decomp.).

EXAMPLE 4

This example illustrates the preparation of methyl 2[5'-(N-acetylmethylaminotetrazol-1'-yl)]benzoate having the structural formula:

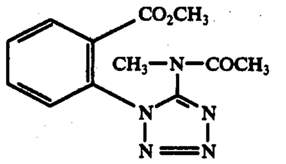

(Compound No 3)

A mixture of methyl 2-isothiocyanato benzoate (19.0 g, prepared as described in *J. Organic Chemistry* 1962, 27, 3701), sodium azide (9.85 g) and water (200 ml) was refluxed, with stirring, for thirty minutes. It was then cooled, filtered through kieselguhr and acidified with dilute hydrochloric acid to give methyl 2(5'-mercaptotetrazol-1'-yl) benzoate (17.28 g, m.p. 147°-8°).

A mixture of this material (11.35 g), sodium hydride (2.12 g, 50% dispersion in mineral oil, pre-washed with petroleum) and dry N,N-dimethylformamide (44 ml) was treated with stirring, at 0°, with N-methylchloroacetamide (5.24 g). It was stirred overnight, poured into ice-water and the precipitate filtered off and dried. Recrystallisation from methanol gave methyl 2[5'-(N-methylacetamido methylthio) tetrazol-1'-yl]benzoate (8.52 g, m.p. 97°-8°).

A mixture of this material (7.0 g), acetic acid (58 ml), 2N sulphuric acid (58 ml) and potassium permanganate (5.8 g) was stirred at 5° for one hour, then decolorised by the addition of sodium metabisulphite. Water was added and the precipitate filtered off and washed with water. Recrystallisation from methanol gave methyl 2[5'-(N-methylacetamidomethanesulphonyl)tetrazol-1'-yl]benzoate (4.66 g, m.p. 138°-9°, decomp.).

A mixture of this material (3.4 g), 1,5-diazabicyclo[4.3.0]non-5-one (1.2 g) and acetonitrile (28 ml) was refluxed for 30 minutes, cooled, diluted with water, acidified with dilute hydrochloric acid and extracted with chloroform. The extract was washed, dried and evaporated and the residue triturated with ether/petroleum and recrystallised from toluene to give the title compound (2.45 g, m.p. 134°).

EXAMPLE 5

This example illustrates the preparation of 4-chloro-2(5'-methylaminotetrazol-1'yl)benzoic acid having the structural formula:

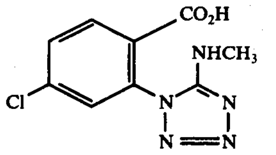

(Compound No 4)

4-chloroanthanilic acid (40 g) was converted, by treatment with hydrogen chloride in methanol, into its methyl ester (27.0 g, m.p. 62°-4°). Successive reactions with thiophosgene, sodium azide, N-methylchloroacetamide and potassium permanganate, basically as described in Example 4, gave methyl 4-chloro-2 [5'-(N-methylacetamidomethanesulphonyl)tetrazol-1'-yl] benzoate (m.p. 152°-4°). Treatment with 1,5-diazabicyclo[4.3.0]non-5-one in acetonitrile (as described in that Example) gave an oily amide-ester which was instantaneously cyclized to 8-chloro-4-methyl-4,5-dihydrotetrazolo[1,5-a]quinazolin-5-one (m.p. 235°-237°) by treatment with sodium hydroxide in methanol. A mixture of this material (800 mg), methanol (4 ml) and N sodium hydroxide solution was refluxed for forty minutes, cooled and filtered. The filtrate was treated with dilute hydrochloric acid to give a precipitate. This was washed with a little ethanol and ether to give the title compound (670 mg, softens 150°, m.p. 224°, decomp.).

EXAMPLE 6

This example illustrates the preparation of methyl 2[5'-(N-acetyl-t-butylamino)tetrazol-1'-yl]benzoate having the structural formula:

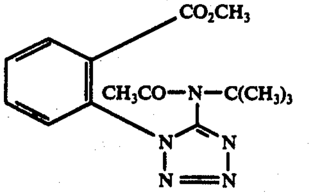

(Compound No 5)

Methyl 2(5-mercaptotetrazol-1'-yl)benzoate, prepared as described in Example 4, was treated successively with N-t-butylchloroacetamide, potassium permanganate and 1,5-diazabicyclo[4.3.0.]non-5-one, basically as described in that Example, to give the title compound, m.p. 125°-6°.

EXAMPLE 7

This example illustrates the preparation of 2-(5'-t-butylaminotetrazol-1'-yl) benzoic acid having the structural formula:

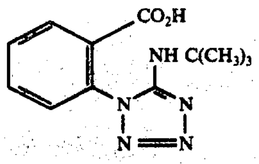

(Compound No 6)

A mixture of methyl 2[5'-N-acetyl-tbutylamino)tetrazol-1'-yl] benzoate (3.0g, prepared as described in Example 6), N sodium hydroxide solution (60 ml) and methanol (30 ml) was refluxed for thirty minutes, cooled, filtered and treated with dilute hydrochloric acid. The precipitate was filtered off, washed with water and ether to give the title compound (2.25g., m.p. 155°).

EXAMPLE 8

This example illustrates the preparation of 2(5'-cyclohexylaminotetrazol-1'-yl) benzoic acid having the structural formula:

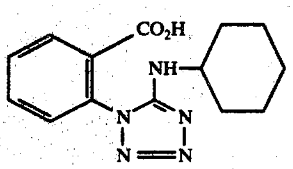

(Compound No 7)

Methyl 2(5'-mercaptotetrazol-1'-yl) benzoate, prepared as described in Example 4, was treated successively with N-cyclohexylchloroacetamide, potassium permanganate, 1,5-diazabicyclo [4.3.0]non-5-ene and sodium hydroxide solution basically as described for a similar compound in Examples 6 and 7. The product, the title compound, had m.p. 123°-4°.

EXAMPLE 9

This example illustrates the preparation of methyl 2(5'-dimethylaminotetrazol-1'-yl) benzoate having the structural formula:

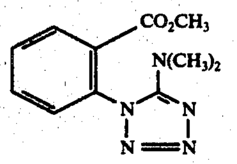

(Compound No. 8)

A cooled mixture of sodium 2(5'-methylaminotetrazol-1'-yl) benzoate (1.8g, prepared as described in Example 3), sodium hydride (0.4 g, 50% dispersion, prewashed with petroleum), methyl iodide (3.0 ml) and N,N-dimethylformamide (15 ml) was stirred for eighteen hours at room temperature, diluted with water and extracted with ether. The extracts were washed well with water, dried and evaporated to give a white residue (0.79g). This was recrystallized from toluene to give the title compound (0.66g., m.p. 128°-130°).

EXAMPLE 10

This example illustrates the preparation of 2(5'-dimethylaminotetrazol-1'-yl) benzoic acid having the structural formula:

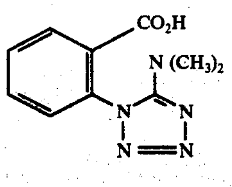

(Compound No. 9)

A mixture of methyl 2(5'-dimethylaminotetrazol-1'-yl) benzoate (234 mg, prepared as described in Example 9) and N sodium hydroxide solution (2.0 ml) was heated on a steam bath, with stirring, for ten minutes. Treatment with dilute hydrochloric acid gave a precipitate (170 mg., m.p. 121°-2°).

Recrystallization from acetonitrile gave the title compound, m.p. 124°, decomp.

EXAMPLE 11

This example illustrates an atomisable fluid comprising a mixture consisting of 25% by weight of Compound No. 1 of Example 1 and 75% by weight of xylene.

EXAMPLE 12

This example illustrates a dusting powder which may be applied directly to plants or other surfaces and comprises 1% by weight of Compound No. 2 of Example 3 and 99% by weight of talc.

EXAMPLE 13

25 Parts by weight of the product described in Example 4, 65 parts by weight of xylene, and 10 parts of an alkyl aryl polyether alcohol ('Triton' X-100; 'Triton' is a Trade Mark) were mixed in a suitable mixer. There was thus obtained an emulsion concentrate suitable for use in agriculture application.

EXAMPLE 14

5 Parts by weight of Compound No. 1 of Example 1 were thoroughly mixed in a suitable mixer with 95 parts by weight of talc. There was thus obtained a dusting powder.

EXAMPLE 15

This example illustrates a concentrated liquid formulation in the form of an emulsion. The ingredients listed below were mixed together in the stated proportions and the whole stirred until the constituents were dispersed.

| | % wt. |
|---|---|
| Compound No. 2 (Example 3) | 20 |
| "Lubrol" L ("Lubrol" is a Trade Mark). | 17 |
| Calcium dodecylbenzenesulphonate | 3 |
| Ethylene dichloride | 45 |
| "Aromasol" H ("Aromasol" is a Trade Mark), | 15 |
| | 100% |

EXAMPLE 16

The ingredients listed below were ground together in the proportions stated to produce a powdered mixture readily dispersible in liquid.

| | % wt. |
|---|---|
| Compound No. 3 (Example 4) | 50 |
| Dispersol T ("Dispersol" is | |

-continued

| | % wt. |
|---|---|
| a Trade Mark). | 5 |
| China Clay | 45 |
| | 100% |

EXAMPLE 17

A composition in the form of grains readily dispersible in a liquid (for example water) was prepared by grinding together the first four of the ingredients listed below in the presence of water and then the sodium acetate was mixed in. The admixture was dried and passed through a British Standard mesh sieve, size 44–100 to obtain the desired size of grains.

| | % wt. |
|---|---|
| Compound No. 7 (Example 8) | 50 |
| Dispersol T | 12.5 |
| Calcium lignosulphonate | 5 |
| Sodium dodecylbenzenesulphonate | 12.5 |
| Sodium acetate | 20 |
| | 100% |

EXAMPLE 18

A composition suitable for use as a seed dressing was prepared by mixing all three of the ingredients set out below in the proportions stated.

| | % wt. |
|---|---|
| Compound No. 1 (Example 2) | 80 |
| Mineral Oil | 2 |
| China Clay | 18 |
| | 100% |

EXAMPLE 19

A granular composition was prepared by dissolving the active ingredient in a solvent, spraying the solution obtained onto the granules of pumice and allowing the solvent to evaporate.

| | % wt. |
|---|---|
| Compound No. 1 (Example 1) | 5 |
| Pumice Granules | 95 |
| | 100% |

EXAMPLE 20

An aqueous dispersion formulation was prepared by mixing and grinding the ingredients recited below in the proportions stated.

| | % wt. |
|---|---|
| Compound No. 7 (Example 8) | 40 |
| Calcium lignosulphonate | 10 |
| Water | 50 |
| | 100% |

The following constitutes an explanation of the compositions or substances represented by the various Trade Marks and Trade Names referred to in the foregoing Examples.

| | |
|---|---|
| "LUBROL" L | is a condensate of 1 mole of nonyl phenol with 13 molar proportions of ethylene oxide. |
| "AROMASOL" H | is a solvent mixture of alkylbenzenes. |
| "DISPERSOL" T | is a mixture of sodium sulphate and a condensate of formaldehyde with the sodium salt of naphthalene sulphonic acid. |
| "LISSAPOL" NX | is a condensate of 1 mole of nonyl phenol with 8 moles of ethylene oxide. |
| "TRITON" X-100 | is an alkyl aryl polyether alcohol. |

EXAMPLE 21

The compounds prepared according to Examples 1 to 9 were tested against a variety of foliar fungal diseases of plant.

The technique employed is to spray the foliage of the undiseased plants with a solution of the test compound and also to drench the soil in which the plants are growing with another solution of the test compound.

All solutions for spraying contained 100 ppm of the test compound. All the soil drench solutions also contained 100 ppm of the test compound.

The plants were then infected with the disease it was desired to control and after a period of days, depending upon the particular disease, the extent of the disease was visually assessed. The results are given below, in the form of a grading as follows:

| Grading | Percentage Amount of Disease |
|---|---|
| 0 | 61 to 100 |
| 1 | 26 to 60 |
| 2 | 6 to 25 |
| 3 | 0 to 5 |
| 4 | 0 |

In the first table below, the disease is given in the first column, whilst in the second column is given the time which elapsed between infecting the plants and assessing the amount of disease. The third column assigns to each disease a code letter, these code letters being used in the second table to identify the diseases.

TABLE 4

| Disease and Plant | Time Interval (days) | Disease Code Letter (Table No 2) |
|---|---|---|
| *Phytophthora infestans* (tomato) | 3 | A |
| *Piricularia oryzae* (rice) | 7 | B |
| *Botrytis cinerea* (Broad bean) | 3 | C |

TABLE 4A

| Compound No | Disease Code Letter (Table 4) | | |
|---|---|---|---|
| Table 1 | A | B | C |
| 1 | 0–1 | 3–4 | 0 |
| 2 | 0 | 3–4 | 0 |
| 3 | 3–4 | 2–4 | 2 |
| 8 | 0 | 3 | 0 |
| 9 | 0 | 1 | 0 |

EXAMPLE 22

This example illustrates the activity of the invention compounds and compositions against the soil-borne fungal diseases *Rhizoctonia solani* and *Pythium ultimum*.

The test chemicals were prepared in the same way as for the foliar sprays and soil drench experiments of Example 21. They were then applied at the rate of 250 parts per million (ppm) to John Innes compost which had been inoculated 24 hours previously with spores of the fungal disease being tested against.

Pots of 1½ inches diameter containing the inoculated soil and lettuce or mustard seeds were placed in 10 milliliters of the solution of the test chemical. After 7 to 8 days seedling emergence was compared with that of a control pot placed in water alone. The results were graded on a scale 0 to 4 where 0 signifies no control of the disease and 4 signifies complete control.

TABLE

| Disease | Compound No. and Disease Grade (parenthetical) | |
|---|---|---|
| *Pythium ultimum* | 2(1), | 7(1) |
| *Rhizoctonia solani* | 2(1), | |

We claim:

1. A tetrazole derivative having the structural formula:

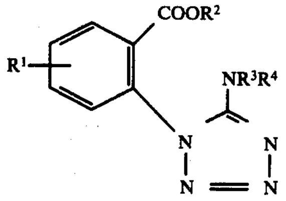

where $R^1$ is hydrogen or chlorine, $R^2$ and $R^3$ are hydrogen or alkyl containing 1 to 4 carbon atoms; $R^4$ is hydrogen, alkyl containing from 1 to 4 carbon atoms, cyclohexyl or acetyl; and salts thereof.

2. A pesticidal composition comprising as an active ingredient a pesticidally effective amount of a tetrazole derivative having the formula:

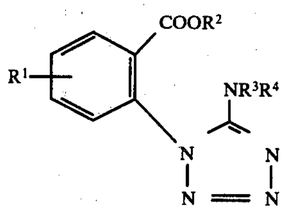

where $R^1$ is hydrogen or chlorine, $R^2$ and $R^3$ are hydrogen or alkyl containing 1 to 4 carbon atoms; $R^4$ is hydrogen, alkyl containing from 1 to 4 carbon atoms, cyclohexyl or acetyl; or a salt thereof together with a carrier for said active ingredient.

3. A process for combating fungi which comprises contacting said fungi or a locus thereof with an effective amount of a tetrazole derivative which has the formula:

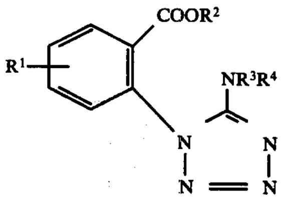

where $R^1$ is hydrogen or chlorine, $R^2$ and $R^3$ are hydrogen or alkyl containing 1 to 4 carbon atoms; $R^4$ is hydrogen, alkyl containing from 1 to 4 carbon atoms, cyclohexyl or acetyl; or a salt thereof.

4. A tetrazole derivative according to claim 1 wherein $R^4$ is methyl.

5. A composition according to claim 2 wherein said tetrazole derivative is one wherein $R^4$ is methyl.

6. A process according to claim 3 wherein said tetrazole derivative is one wherein $R^4$ is methyl.

7. A tetrazole derivative according to claim 1 wherein $R^1$ and $R^2$ are hydrogen, $R^3$ is hydrogen and $R^4$ is methyl.

* * * * *